(12) United States Patent
Cole et al.

(10) Patent No.: US 6,607,735 B2
(45) Date of Patent: Aug. 19, 2003

(54) METHOD FOR REDUCING THE APPEARANCE OF DARK CIRCLES UNDER THE EYES

(75) Inventors: Curtis Cole, Ringoes, NJ (US); Irina Ganopolsky, Lawrenceville, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/742,920

(22) Filed: Dec. 21, 2000

(65) Prior Publication Data

US 2002/0119172 A1 Aug. 29, 2002

(51) Int. Cl.[7] .......................... A61L 7/00; A61L 31/045; A01N 33/18; A01N 33/24; A01N 31/04
(52) U.S. Cl. ........................ 424/401; 514/724; 514/727; 514/740; 514/844
(58) Field of Search .................... 424/401; 514/724, 514/727, 740, 844

(56) References Cited

U.S. PATENT DOCUMENTS

| | | | |
|---|---|---|---|
| 3,875,198 A | 4/1975 | Strobel | 260/404.5 |
| 3,878,229 A | 4/1975 | Strobel | 260/404.5 |
| 4,199,562 A | 4/1980 | Vanlerberghe et al. | 424/47 |
| 4,224,339 A | 9/1980 | Van Scott et al. | 424/289 |
| 4,283,386 A | 8/1981 | Van Scott et al. | 424/70 |
| 4,491,534 A | 1/1985 | Vanlerberghe et al. | 252/357 |
| 4,620,037 A | 10/1986 | Vanlerberghe et al. | 568/36 |
| 4,885,157 A * | 12/1989 | Fiaschetti | 424/59 |
| 4,888,437 A | 12/1989 | Zeidler et al. | 558/105 |
| 4,971,789 A | 11/1990 | Vanlergerghe et al. | 424/70 |
| 5,204,105 A * | 4/1993 | Mausner | 424/401 |
| 5,352,389 A | 10/1994 | Gazzani | 252/544 |
| 5,554,647 A | 9/1996 | Perricone | 514/474 |
| 5,574,063 A | 11/1996 | Perricone | 514/474 |
| 5,607,691 A | 3/1997 | Hale et al. | 424/449 |
| 5,643,586 A | 7/1997 | Perricone | 424/401 |
| 5,747,049 A | 5/1998 | Tominaga | 424/70 |
| 5,856,357 A | 1/1999 | Yu et al. | 514/557 |
| 5,879,690 A | 3/1999 | Perricone | 424/401 |
| 6,015,575 A | 1/2000 | Luther et al. | 424/450 |
| 6,017,556 A | 1/2000 | Luther et al. | 424/450 |
| 6,068,847 A | 5/2000 | Aleles et al. | 424/401 |

FOREIGN PATENT DOCUMENTS

| | | |
|---|---|---|
| EP | 0 158 090 | 8/1990 |
| EP | 0396857 A1 | 11/1990 |
| EP | 0 343 694 | 11/1992 |
| EP | 0 649 834 | 4/1995 |
| EP | 1192939 A | 4/2001 |
| FR | 2 504 530 | 4/1981 |
| FR | 2 604 625 | 10/1986 |
| FR | 2 648 132 | 6/1989 |
| GB | 1182320 | 12/1968 |
| JP | 60-9517 | 1/1985 |
| JP | 4-95008 | 3/1992 |
| JP | 5-58971 | 3/1993 |
| JP | 6-145134 | 5/1994 |
| JP | 6-247826 | 9/1994 |
| JP | 7-223920 | 8/1995 |
| JP | 11335236 A | 7/1999 |
| JP | WO 99/45900 | 9/1999 |
| WO | WO 98/23152 | 6/1998 |
| WO | WO 99/06431 | 2/1999 |
| WO | WO 99/06437 | 2/1999 |
| WO | WO 99/45922 | 9/1999 |
| WO | WO 00/01351 | 1/2000 |
| WO | WO 00/27353 | 5/2000 |
| WO | WO 0185129 A | 11/2001 |

OTHER PUBLICATIONS

U.S. patent application Ser. No. 09/677,738, filed Oct. 2, 2000.
U.S. patent application Ser. No. 09/677,737, filed Oct. 2, 2000.
U.S. patent application Ser. No. 60/237,230, filed Oct. 2, 2000.
U.S. patent application Ser. No. 09/742,622, filed Dec. 21, 2000.
European Search Report, EP01310849, Sep. 11, 2002.

* cited by examiner

*Primary Examiner*—Jose' G. Dees
*Assistant Examiner*—Marina Lamm
(74) *Attorney, Agent, or Firm*—Erin M. Harriman

(57) ABSTRACT

The invention relates to a method for the treatment of the skin around the eyes of a mammal, in particular a method for reducing the puffiness of and the appearance of dark circles on the skin under the eyes. The method comprises topically applying to the affected skin area a composition comprising an effective amount of at least one alkanolamine having the following general formula:

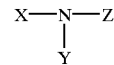

wherein X, Y and Z are selected from the group consisting of hydrogen, $C_1$–$C_3$ alkyl group, $C_2$–$C_4$ alkanol group, wherein at least one of X, Y or Z is a $C_2$–$C_4$ alkanol group bearing at least one hydroxyl group and optionally at least one carboxyl group.

9 Claims, No Drawings

METHOD FOR REDUCING THE APPEARANCE OF DARK CIRCLES UNDER THE EYES

FIELD OF THE INVENTION

This invention relates to compositions and methods for treating the skin under they eyes of mammal. More particularly, it relates to compositions containing at least one compound selected from an alkanolamine and/or tyrosine and their application to mammalian skin. The compositions can be applied to skin to effect a reduction in the puffiness of skin under the eyes and the appearance of dark circles around the eyes, in particular, under the eyes.

BACKGROUND OF THE INVENTION

Human beings have long sought products that can enhance the appearance of the skin and reduce the signs of stress and aging without cosmetic surgery. The skin around the eye is relatively thin and contains less fat than most other areas of skin. For this reason, a widespread cosmetic problem is the appearance of puffy or pouch-like skin, bags, rings or dark circles beneath the eyes. These conditions can be caused by stress, lack of sleep, overindulgence with alcohol, aging, various diseases, and other environmental factors that irritate the eyes and the surrounding skin.

It is believed that the dark circles on the skin around the eye is a result of temporary blood pooling or stasis which is exacerbated at night when lying prone when the blood vessels around the eye are subjected to higher blood pressure relative to an upright (daytime activity) posture. Overnight, the blood in the venous side of the circulatory system pools in the rich vascular bed under the eye due to the higher resistance to flow when prone, resulting in a dark appearance of the area under the eye particularly evident upon rising in the morning. Most products designed for treating dark circles are tinted with pigments of various colors to cover over or offset the dark of the dark circles and reflect incident light. They merely cover the existing dark circles. Another approach is to use products containing cell stimulants such as retinoids to attempt to thicken the skin over the area to hide the darker blood rich skin beneath. Such products require weeks to become effective, and are often irritating to the sensitive skin around the eyes.

Thus, it is an object of this invention to provide topical compositions that can be used to ameliorate puffiness and improve the appearance of dark circles of mammalian skin surrounding the eyes immediately (within 30–60 minutes) after application.

It is another object of this invention is to provide topical compositions to ameliorate puffiness and the appearance of dark circles that is well-tolerated by the skin.

SUMMARY OF THE INVENTION

It has been discovered that compositions containing at least one compound selected from an alkanolamine can be used to alleviate the puffiness and dark circles of mammalian skin, in particular skin around the eyes.

Accordingly, in one embodiment, the invention relates to a method treating the skin around the eyes of a mammal, said method comprising topically applying to the skin a composition comprising an effective amount of at least one alkanolamine. The alkanolamine has the following general formula:

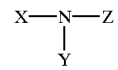

wherein X, Y and Z are selected from the group consisting of hydrogen, $C_1$–$C_3$ alkyl group, $C_2$–$C_4$ alkanol group, wherein at least one of X, Y or Z is a $C_2$–$C_4$ alkanol group bearing at least one hydroxyl group and optionally at least one carboxyl group.

DETAILED DESCRIPTION OF THE PREFERRED EMBODIMENTS

As discussed above, the invention relates to a method for treating the skin around the eyes, in particular, the skin under the eyes. In particular, the invention relates to a method for reducing the appearance of dark circles and puffiness of the skin around the eye. The method comprises topically applying to the affected skin area, a composition comprising an effective amount of at least one alkanolamine. The alkanolamine has the following general formula:

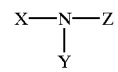

wherein X, Y and Z are selected from the group consisting of hydrogen, $C_1$–$C_3$ alkyl group, $C_2$–$C_4$ alkanol group, wherein at least one of X, Y or Z is a $C_2$–$C_4$ alkanol group bearing at least one hydroxyl group and optionally at least one carboxyl group.

In a preferred embodiment the alkanolamine is selected from the group consisting of ethylaminoethanol, methylaminoethanol, dimethylaminoethanolamine, isopropanolamine, triethanolamine, isopropanoldimethylamine, ethylethanolamine, 2-butanolamine, choline and serine. More preferably, the alkanolamine is dimethylaminoethanol (DMAE).

The compositions used in the methods according to the invention preferably contain from about 0.1 about 10% by weight of the at least one alkanolamine, more preferably, from about 0.1 to about 5% and, most preferably, from about 1 to about 3% by weight.

In a preferred embodiment, the compositions used in the methods of the invention contain a pH buffering agent. Preferably, the amount of buffering agent should be that which would result in compositions having a pH ranging from about 4.5 to about 8.5, more preferably from about 5.5 to about 8.5, most preferably from about 6.5 to about 8.0. The buffering agent can be any of the known buffering agents commonly found in cosmetic compositions provided that they are physically and chemically stable with the other ingredients of the composition. Suitable buffering agents include organic acids such as (but not intended to be restricted to) citric acid, malic acid, and glycolic acid.

Another compound which is advantageously present in the compositions of this invention is tyrosine. Tyrosine may be present in the compositions of this invention in the amount of from about 0.01 to about 5%, more preferably from about 0.04 to about 3% by weight and most preferably about 0.5% by weight, based on the total composition.

The compositions of this invention should be in the form of topical products that can be applied externally to the skin and can be prepared in accordance with conventional techniques known to those of ordinary skill in the art. The carrier may take a variety of physical forms such as, for example, creams, dressings, gels, lotions, ointments or liquids, including leave on and rinse-off compositions, as well as incorporated into material carriers such as dry or wet wipes, puffs, hydro-gel matrixes, or adhesive (or non-adhesive) patches by means known in the art. Preferably, the carrier should be a gel or moisturizing lotion, a cooling solution, or in the form of a dry or wet wipe. One could also utilize this in a convenient spray applicator.

Typical carriers include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as cosmetically acceptable carriers. Preferably, the carrier should be a gel base formula without lipid materials that would exxacerbate the oiliness of acne prone skin. However, a moisturizer emulsion base may be preferred by individuals that have particularly dry yet skin still suffer from acne lesions.

The topical compositions according to the invention can comprise additional ingredients commonly found in skin care compositions, such as for example, emollients, skin conditioning agents, emulsifying agents, humectants, preservatives, antioxidants, perfumes, chelating agents, etc., provided that they are physically and chemically compatible with the other components of the composition. It is also envisioned that this invention could be combined with other agents such as topical anesthetics (such as benzocaine or other caine type molecules) or even mild steroids such as hydrocortisone for enhanced anti-inflammatory activity]. This invention could also be combined with other natural extracts or oils that have intrinsic anti-inflammatory or analgesic properties. Notably useful for long term treatment of this problem is the incorporation of vitamin A and vitamin A derivatives, including but not restricted to retinoids, such as, retinol, retinyl palmitate, retinoic acid, retinal, and retinyl propionate.

Examples of suitable preservatives for use in the compositions of the invention include the $C_1$–$C_4$ alkyl parabens and phenoxyethanol. Generally, the preservative is present in an amount ranging from about 0.5 to about 2.0, preferably about 1.0 to about 1.5, weight percent based on the total composition. In a preferred embodiment, the preservative is mixture of from about 0.2 to about 0.5 weight percent methylparaben, from about 0.2 to about 5.0 weight percent propylparaben and from about 0.05 to about 0.10 weight percent butylparaben. A particularly preferred commercially available preservative that may be used in the skin care composition according to this invention is PHENONIP TM which is a practically colorless, viscous, liquid mixture of phenoxyethanol, methylparaben, ethylparaben, propylparaben, and butylparaben available from Nipa Laboratories, Inc., Wilmington, Del.

Preferably, antioxidant should be present in the compositions according to the invention. Suitable antioxidants include butylated hydroxy toluene (BHT), ascorbyl palmitate, butylated hydroanisole (BHA), phenyl-α-naphthylamine, hydroquinone, propyl gallate, nordihydroquiaretic acid, vitamin E or derivatives of vitamin E, vitamin C and derivatives thereof, calcium pantothenic, green tea extracts and mixed polyphenosls, and mixtures thereof. Of the above, the most preferred antioxidant is BHT. Preferably, the antioxidant present in the composition at from about 0.02 to about 0.05% by weight, most preferably from about 0.02 to about 0.10% by weight.

Emollients which can be included in the compositions of the invention function by their ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 cetyl ether, steareth-10, oleth-8, PPG-4 lauryl ether, vitamin E acetate, PEG-7 glyceryl cocoate, lanolin, cetyl alcohol, octyl hydroxystearate, dimethicone, and combinations thereof. Cetyl alcohol, octyl hydroxystearate, dimethicone, and combinations thereof are preferred. When utilized, the emollient can be present in an amount from about 0.01 to about 5, preferably from about 1 to about 4% by weight of the composition.

Polyhydric alcohols can be utilized as humectants in the compositions of the invention. The humectants aid in increasing the effectiveness of the emollient, reduce scaling, stimulate removal of built-up scale and improve skin feel. Suitable polyhydric alcohols include, but are not limited to, glycerol (also known as glycerin), polyalkylene glycols, alkylene polyols and their derivatives, including butylene glycol, propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof. Glycerin is preferred. When utilized, the humectant is present in an amount from about 0.1 to about 5, preferably from about 1 to about 3 percent by weight, based on the total weight of the composition.

The compositions according to the invention preferably contain an effective stabilizing amount of an emulsifier. Preferably, the emulsifier is present at from about 1.0 to about 10.0, more preferably from about 3.0 to about 6.0, weight percent, based on the total composition. Any emulsifier that is compatible with the components of the composition can be employed. Suitable emulsifiers include stearic acid, cetyl alcohol, stearyl alcohol, steareth 2, steareth 20, Acrylates/C10–30 alkyl Acrylate Crosspolymer. Particularly preferred is PEMULEN TR-1 (CTFA Designation: Acrylates/10–30 Alkyl Acrylate Crosspolymer).

Any fragrance may be added to the compositions of the invention for aesthetic purposes. Suitable fragrances include, but are not limited to, eucalyptus oil, camphor synthetic, peppermint oil, clove oil, lavender, chamomile and the like. When utilized, fragrances are present in an amount from about 0.05 to about 0.5, preferably from about 0.1 to about 0.3 percent by weight, based on the total weight of the composition.

In certain aspects of this invention, the compositions should include a chelating agent. Chelating agents which are useful in the compositions of the present invention include ethylenediamine tetra acetic acid (EDTA) and derivatives and salts thereof, dihydroxyethyl glycine, tartaric acid, and mixtures thereof. The chelating agents should be utilized in a stabilizing effective amount and may range from about 0.01 to about 2% based on the weight of the total composition, preferably from about 0.05 to about 1%. Most preferably, the chelating agent should be EDTA.

Generally, the composition is topically applied to the affected skin areas in a predetermined or as-needed regimen to bring about improvement, it generally being the case that beyond the immediate improvement seen upon initial use for reduction of dark circles, improvement is also noted for reduction of puffiness of the eyes with repeated application. Insofar as has been determined based upon clinical studies to date, no adverse side effects are encountered.

The advantages of the invention and specific embodiments of the skin care compositions prepared in accordance with the present invention are illustrated by the following examples. It will be understood, however, that the invention is not confined to the specific limitations set forth in the individual examples, but rather defined within the scope of the appended claims.

EXAMPLES

The following materials were used in the Examples that follow:

BRIJ 72: steareth 2 emulsifier commercially available from Uniqema.
BRIJ 721: steareth 20 emulsifier commercially available from Uniqema.
DIMETHICONE 47V-100: dimethicone 100 centistokes emollient commercially available form Rhodia.
PEMULEN TR1: acrylates/10–30 alkyl acrylate crosspolymer commercially available from BF Goodrich.
PHENONIP: mixture of phenoxyethanol, methylparaben, ethylparaben, propylparaben, and butylparaben commercially available from Nipa Laboratories, Inc.
STABILIEZE QM: PVM/MA decadiene crosspolymer commercially available from ISP Technologies.

Example 1

The following formula was made in accordance with the teachings of this invention.

Deionized water was added to a kettle and heated to about 78 to about 80° C. At about 78 to about 80° C., STABILEZE QM was added using a propeller mixer. The mixture was held at about 78 to about 80° C. until clear. Heating was discontinued and when the mixture was at about 75° C., disodium EDTA was added. At about 40° C., the tyrosine/DMAE premix was added to the mixture and mixed well. The DMAE/tyrosine premix was prepared as follows: deionized water, DMAE, and tyrosine were added to a closed container and placed in a heated (50-50° C.) water bath. The mixture was heated to about 50 to about 55° C. The mixture was held at that temperature with mixing until the tyrosine dissolved.

The pH of the mixture was adjusted to about 7.0 to about 7.5 with the glycolic/malic buffer premix. The remaining ingredients were added with mixing in the following order: Silicone Quarternium-13, ethanol, PHENONIP. The mixture was homogenized at 40% for about 3–4 minutes with a rotor-stator homogenizer.

| INGREDIENT: | WEIGHT PERCENT: |
|---|---|
| Water Phase: | |
| Deionized water | 88.92 |
| STABILEZE QM | 1.10 |
| Disodium EDTA | 0.10 |
| DMAE/Tyrosine Premix: | |
| L-tyrosine | 0.04 |
| DMAE | 3.00 |
| Buffer Premix: | |
| Glycolic acid (70 wt. % aqueous solution) | 1.2 |
| Malic acid | 0.84 |
| Deionized water | 1.32 |
| Other Additives: | |
| Silicone Quarternium-13 | 1.00 |
| Ethanol | 0.5 |
| PHENONIP | 1.00 |

Example 2

The following formula was made in accordance with the teachings of this invention.

Deionized water was added to a kettle and heated to 78° C. In the process of heating the following ingredients were added: disodium EDTA, glycerin, panthenol, phenoxyethanol. At 78° C. methylparaben and propylparaben were added. The mixture was held at medium speed mixing for phasing.

In a separate kettle the following ingredients were combined: FINSOLV TN, WICKENOL 171, DIMETHICONE 47v-100, BRIJ 72, cetal alcohol, BRIJ 721, BHT. The mixture was heated and when it was homogenous, PEMULEN was added. The agitation was at high speed. When both phases were at 78° C., oil phase was added to water phase slowly while mixing turbulently. The temperature was held for 10–15 minutes and mixing continued until an emulsion was formed. After that, the heat was discontinued.

At 45° C. or below the mixture of L-Tyrosine and 2-(dimethylamino)ethanol was added to the batch and mixed well. Then, a mixture of glycolic and malic acids was added to adjust pH to 7.0. Finally, the product was homogenized for 3–4 minutes at high power.

| INGREDIENT: | WEIGHT PERCENT: |
|---|---|
| Water Phase: | |
| Deionized water | 62.69 |
| Disodium EDTA | 0.10 |
| Glycerin | 3.00 |
| Panthenol | 0.50 |
| Phenoxyethanol | 0.73 |
| Methylparaben | 0.35 |
| Propylparaben | 0.17 |
| DMAE/L-Tyrosine pre-mix | |
| L-tyrosine | 0.50 |
| DI Water | 15.00 |
| DMAE | 3.00 |
| Buffer Premix: | |
| Glycolic acid (70 wt. % aqueous solution) | 1.2 |
| Malic acid | 0.84 |
| Deionized water | 1.32 |

| INGREDIENT: | WEIGHT PERCENT: |
|---|---|
| Oil Phase | |
| C12-15 Alkyl Benzoate | 4.00 |
| Octyl Hydroxystearate | 1.00 |
| Dimethicone 47v-100 | 1.00 |
| Steareth 2 | 0.60 |
| Cetyl Alcohol | 2.50 |
| Steareth 20 | 0.90 |
| BHT | 0.10 |
| PEMULEN TR1 | 0.50 |

Clinical Evaluations

The ability of the invention to reduce dark circles and puffiness around the eyes was demonstrated in two separate clinical studies. In the first study, 25 women subjects with mild to moderate dark circles under their eyes were recruited for the study. Both an expert grader and the panelists evaluated the severity of the dark circles under their eyes prior to application of test products. The composition of Example 1 was topically applied to the skin area around one eye and a composition not containing the inventive elements (placebo without dimethylaminoethanol or tyrosine) around the opposite eye. Treatment assignments were randomized across the panel, and neither the panelist or the grader had knowledge of the treatment code. One hour after product application, both the grader and panelist separately evaluated the appearance of the dark circles under the eyes. For subjects exhibiting notable differences between the two treatments, there was a significantly higher rating of the eye treated with the inventive elements compared with the placebo ($p \leq 0.88$). Similarly, the expert grader noted reduced dark circles for almost twice as many eyes treated with the active compared with the placebo treated eyes ($p \leq 0.87$).

In a second study, another 25 subjects, 20–30 years of age, were recruited and given choice of products as described in Example 1 or Example 2 depending on their skin type (oily or dry). The panelists assessed the state of puffiness of their own eyes, and were also graded by a dermatologist. The panelists used the product for 4 weeks, returning at week 2 for another dermatologist evaluation. After 2 and 4 weeks of product use, both the panelists and the dermatologist noted significant improvement in the puffiness of the eyes ($p < 0.05$) compared with the baseline observations.

What is claimed is:

1. A method for reducing the appearance of dark circles around the eyes of a mammal, said method comprising the step of:
topically applying on said dark circles a composition comprising an effective amount of at least one alkanolamine of the following general formula:

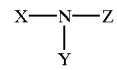

wherein X, Y and Z are selected from the group consisting of hydrogen, $C_1$–$C_3$ alkyl group, $C_2$–$C_4$ alkanol group, wherein at least one of X, Y or Z is a $C_2$–$C_4$ alkanol group bearing at least one hydroxyl group and optionally at least one carboxyl group; and wherein said dark circles are caused by temporary pooling of blood around said eyes.

2. A method according to claim 1, wherein said alkanolamine is selected from the group consisting of ethylaminoethanol, methylaminoethanol, dimethylaminoethanolamine, isopropanolamine, triethanolamine, isopropanoldimethylamine, ethylethanolamine, 2-butanolamine, choline and serine.

3. A method according to claim 2, wherein said alkanolamine is dimethylamino-ethanol.

4. A method according to claim 1, wherein said alkanolamine is present in an amount of from about 0.1 to about 10% by weight of the composition.

5. A method according to claim 4, wherein said composition comprises from about 1 to about 5% by weight of alkanolamine.

6. A method according to claim 1, wherein said composition further comprises tyrosine.

7. A method according to claim 6, wherein said tyrosine is present in an amount of from about 0.01 to about 5% by weight of the composition.

8. A method according to claim 7, wherein said tyrosine is present in an amount of from about 0.04 to about 3% by weight of the composition.

9. A method according to claim 8, wherein said tyrosine is present in an amount of form about 0.04 to about 0.5% by weight of the composition.

* * * * *